(12) United States Patent
Asaoka

(10) Patent No.: US 12,251,082 B2
(45) Date of Patent: Mar. 18, 2025

(54) ENDOSCOPE AND METHOD FOR OPERATING ENDOSCOPE

(71) Applicant: OLYMPUS CORPORATION, Hachioji (JP)

(72) Inventor: Nobuyoshi Asaoka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 160 days.

(21) Appl. No.: 17/942,568

(22) Filed: Sep. 12, 2022

(65) Prior Publication Data
US 2023/0000332 A1 Jan. 5, 2023

Related U.S. Application Data

(63) Continuation of application No. PCT/JP2020/010869, filed on Mar. 12, 2020.

(51) Int. Cl.
A61B 1/06 (2006.01)
A61B 1/00 (2006.01)

(52) U.S. Cl.
CPC ............ A61B 1/06 (2013.01); A61B 1/00009 (2013.01); A61B 1/0655 (2022.02)

(58) Field of Classification Search
CPC .................... A61B 1/0655; A61B 1/00009
See application file for complete search history.

(56) References Cited

U.S. PATENT DOCUMENTS

| | | | |
|---|---|---|---|
| 2008/0242931 A1 | 10/2008 | Nishino | |
| 2009/0187077 A1* | 7/2009 | Hosoda | A61B 1/0669 600/178 |
| 2009/0203964 A1 | 8/2009 | Shimizu et al. | |
| 2017/0231472 A1 | 8/2017 | Nishio et al. | |
| 2021/0113059 A1 | 4/2021 | Kasumi | |
| 2021/0208383 A1 | 7/2021 | Yamazaki | |

FOREIGN PATENT DOCUMENTS

| | | | | |
|---|---|---|---|---|
| CN | 106037845 A | * | 10/2016 | ....... A61B 17/00234 |
| JP | 2000147389 A | * | 5/2000 | |
| JP | 2003-144385 A | | 5/2003 | |
| JP | 2008-091147 A | | 4/2008 | |
| JP | 2008-237639 A | | 10/2008 | |
| JP | 2009-189475 A | | 8/2009 | |
| JP | 2011-24739 A | | 2/2011 | |
| JP | 4624687 B2 | * | 2/2011 | |
| JP | 2016002201 A | * | 1/2016 | |
| JP | 7034308 B2 | | 3/2022 | |
| WO | 2016/071991 A1 | | 5/2016 | |
| WO | 2019/198364 A1 | | 10/2019 | |

OTHER PUBLICATIONS

May 26, 2020 International Search Report issued in International Patent Application No. PCT/JP2020/010869.
Kato, R. et al., "Dependence of the Basic Characteristics of an Eddy Current Sensor on the Area of the Target," Faculty of Engineering, Shinshu University, vol. 20, No. 2, 1996.

* cited by examiner

Primary Examiner — Rowina J Cattungal
(74) Attorney, Agent, or Firm — Oliff PLC

(57) ABSTRACT

An endoscope includes a sensor that can detect a conductive member. Based on a detection result of the conductive member by the sensor, the endoscope can switch between a normal operation mode and an energy-saving operation mode in which power consumption is smaller than power consumption in the normal operation mode.

20 Claims, 5 Drawing Sheets

ENDOSCOPE AND METHOD FOR OPERATING ENDOSCOPE

CROSS REFERENCE TO RELATED APPLICATIONS

This is a Continuation Application of PCT Application No. PCT/JP2020/010869, filed Mar. 12, 2020, which was not published under PCT Article 21(2) in English.

BACKGROUND

Technical Field

The disclosure of the present description relates to an endoscope and a method for operating an endoscope.

Description of the Related Art

Use of an endoscope which enables early detection and treatment of a lesion has been expanded mainly in medical fields. In addition, in recent years, a wireless endoscope which can solve the problem of cumbersome handling of a cable has also been attracting attention.

The wireless endoscope wirelessly transmits images of a test object, which is irradiated with illumination light from a built-in light source, to a video processor. Since in the wireless endoscope, a cable between peripherals such as a video processor and a light source device and the endoscope can be omitted, significant improvement in operability has been expected.

On the other hand, the wireless endoscope receives power supply from a built-in battery, instead of commercial power supply. Therefore, in order to avoid battery exhaustion during endoscope examination, more sophisticated management for power consumption is demanded of the wireless endoscope than of the conventional type endoscope which is connected with the commercial power supply in a wired manner.

In a known power supply management of an endoscope, turning ON/OFF of a lamp is switched by detecting change in capacitance, caused when an operator grips the endoscope, between electrodes which are provided for the endoscope.

SUMMARY

An endoscope according to one aspect of the present disclosure includes: a sensor that can detect a conductive member; and a processor configured to switch between a normal operation mode and an energy-saving operation mode in which power consumption is smaller than power consumption in the normal operation mode based on a detection result of the conductive member by the sensor.

In one non-limiting embodiment, the sensor may be an eddy current sensor that can detect eddy induced currents generated in the conductive member. The eddy current sensor includes a sensor coil, and a coil diameter of the sensor coil may be larger than an internal diameter of a forceps port that opens at a leading end of an insertion part of the endoscope.

A method for operating an endoscope according to one aspect of the present disclosure, includes: detecting, by one or more proximity sensors contained by the endoscope, a conductive member; and switching, by a control part contained by the endoscope, between a normal operation mode and an energy-saving operation mode in which power consumption is smaller than power consumption in the normal operation mode based on a detection result of the conductive member by the one or more proximity sensors.

DESCRIPTION OF THE EMBODIMENTS

In power supply management, inhibiting useless power consumption is important, and equivalently therewith, surely supplying necessary electric power is also important, and in particular, in endoscope examination, a situation in which electric power is shut off at timing which is different from timing which an operator intends is to be avoided.

In addition, although in terms of correctly reflecting the intention of the operator, power supply management using a manual switch, which is conventionally performed in general, is also effective, there may be a case where with priority given to convenience, the manual power supply management is shunned, and furthermore, human error such as forgetting to turn off a power source is easily caused.

It is to be noted that although the wireless endoscope is described as an example, also in the conventional type endoscope using the commercial power supply, similarly, appropriate power supply management is demanded.

Figure 1:
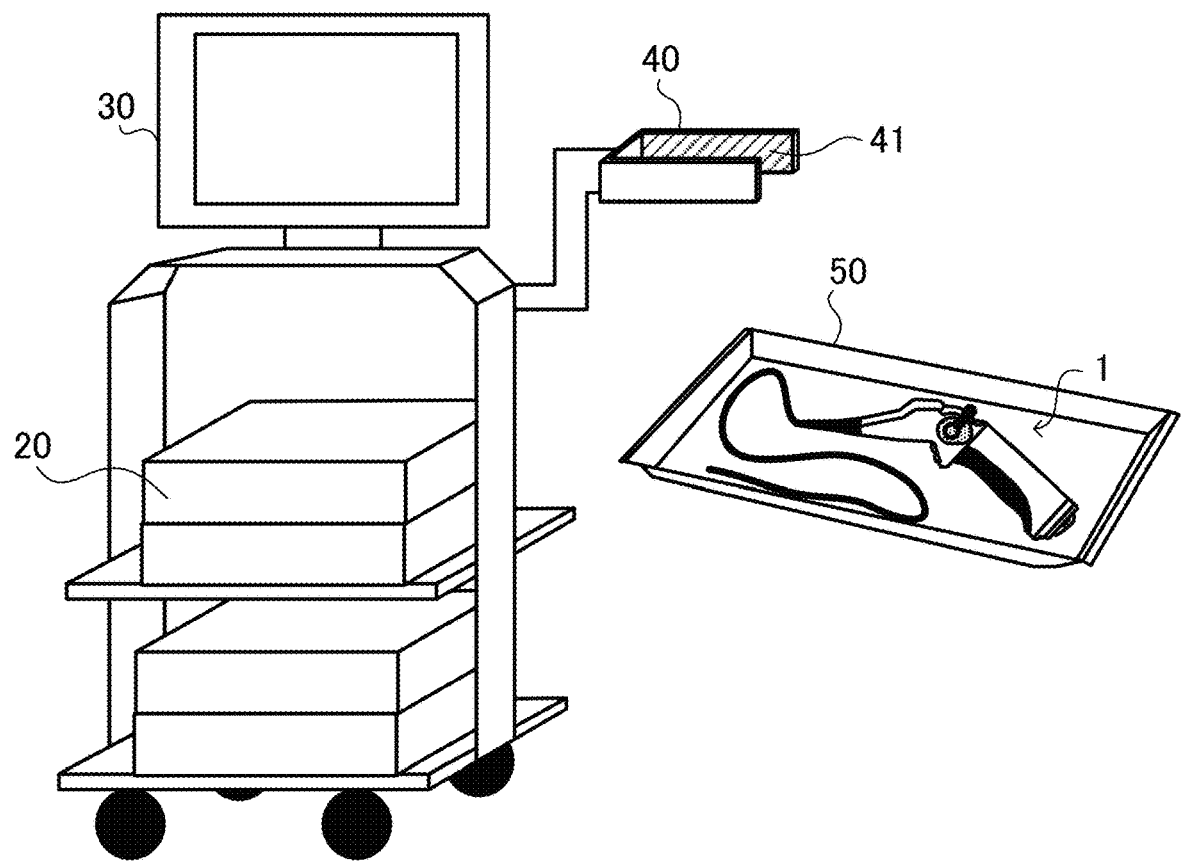
FIG. 1 is a diagram illustrating a configuration of an endoscope system.
Figure 2:
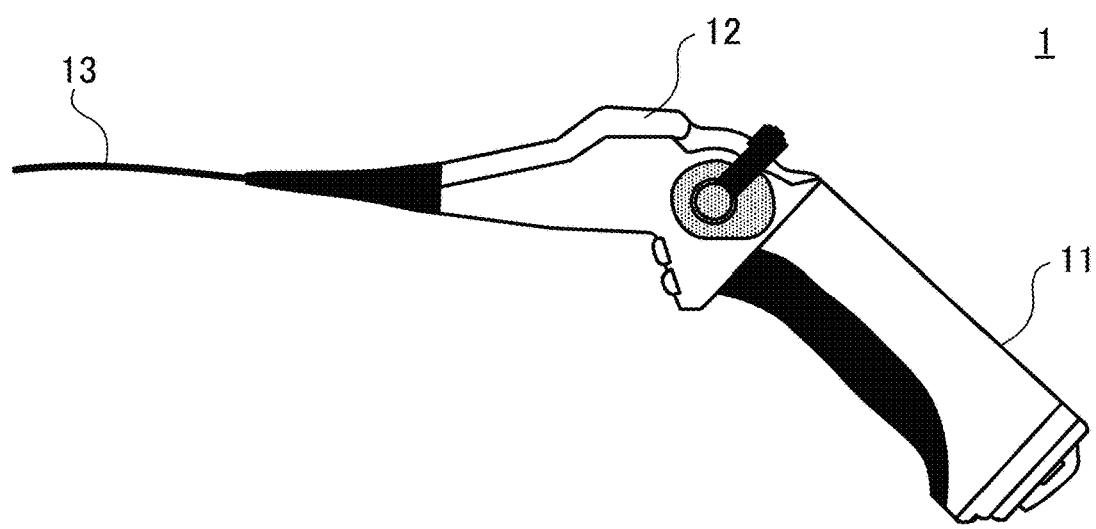
FIG. 2 is a diagram illustrating an appearance configuration of an endoscope.

FIG. 1 is a diagram illustrating a configuration of an endoscope system. FIG. 2 is a diagram illustrating an appearance configuration of an endoscope. Hereinafter, with reference to FIGS. 1 and 2, a configuration of the endoscope system 100 will be described.

As shown in FIG. 1, the endoscope system 100 includes an endoscope 1 and a video processor 20. The endoscope system 100 may further include a monitor 30, an endoscope hanger 40, and a tray 50.

The endoscope 1 is a video scope which includes an image sensor. Although the endoscope 1 is not particularly limited, the endoscope 1 is, for example, a flexible endoscope used for examination and treatment of a nose, ears and throat. In addition, the endoscope 1 may be a rigid endoscope. The endoscope 1 may be an endoscope used for examination and treatment of other organs, for example, a respiratory system such as bronchi or may be an endoscope used for examination and treatment of a digestive system. Alternatively, the endoscope 1 may be an endoscope used for laparoscopic surgery. Furthermore, the endoscope 1 is not limited to the medical endoscope and may be an industrial endoscope.

As shown in FIG. 2, the endoscope 1 includes a grip part 11 which an operator grips, an operation part 12 which the operator operates, and an insertion part 13 which is inserted into a test object. It is to be noted that the endoscope 1 is the so-called wireless endoscope and wirelessly transmits, to the video processor 20, a signal obtained by imaging the test object with the insertion part 13 inserted into a body cavity of the test object (hereinafter, referred to as an endoscopic image). Therefore, the endoscope 1 does not have any universal cord which extends from the operation part 12 and is connected to peripherals such as the video processor 20. However, the endoscope 1 is not limited to the wireless endoscope and may be a wired endoscope which includes a universal cord.

The video processor 20 is a video processor which processes the endoscopic image obtained by the endoscope 1. The video processor 20 converts, for example, the signal from the endoscope 1 to a video signal and outputs the video signal to the monitor 30. Thus, on the basis of the video signal from the video processor 20, the monitor 30 displays a live image.

Although the monitor 30 is, for example, a liquid crystal display, the monitor 30 may be other display device such as an organic EL display. The endoscope hanger 40 is a tool which hangs and retains the endoscope 1, and at least one part thereof is configured by a conductive member 41. The tray 50 is a metallic tray on which the endoscope 1 is placed.

Figure 3:
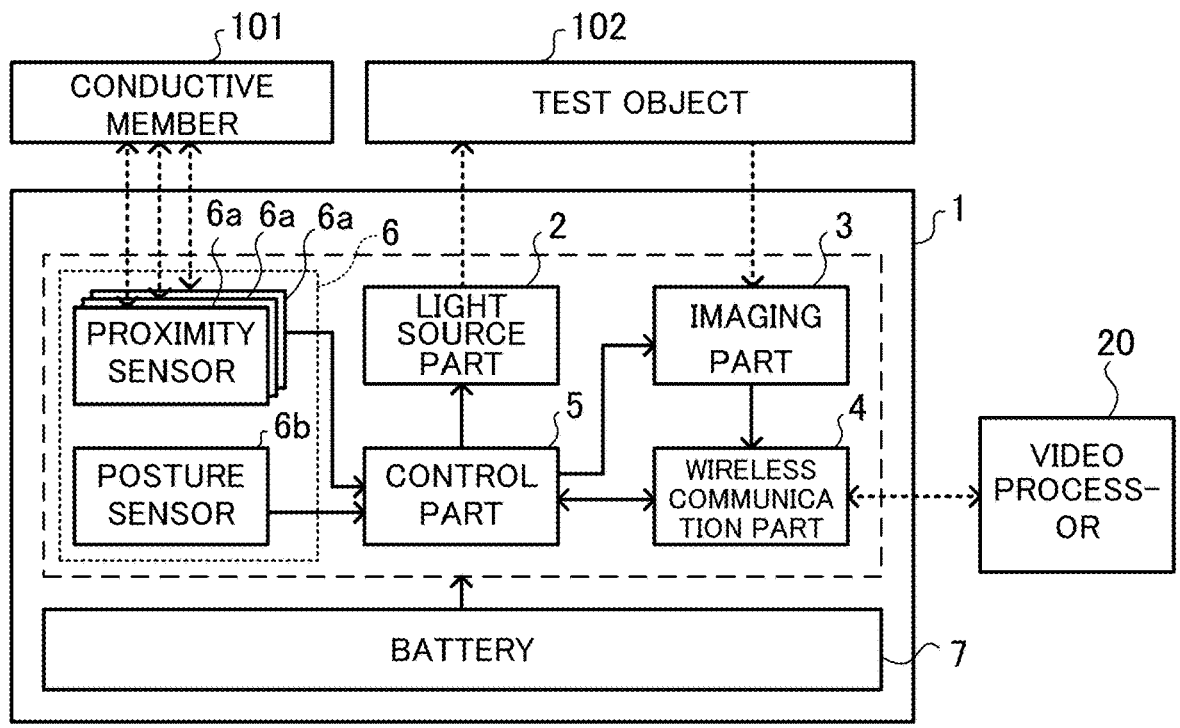
FIG. 3 is a diagram illustrating an internal configuration of the endoscope.
Figure 4:
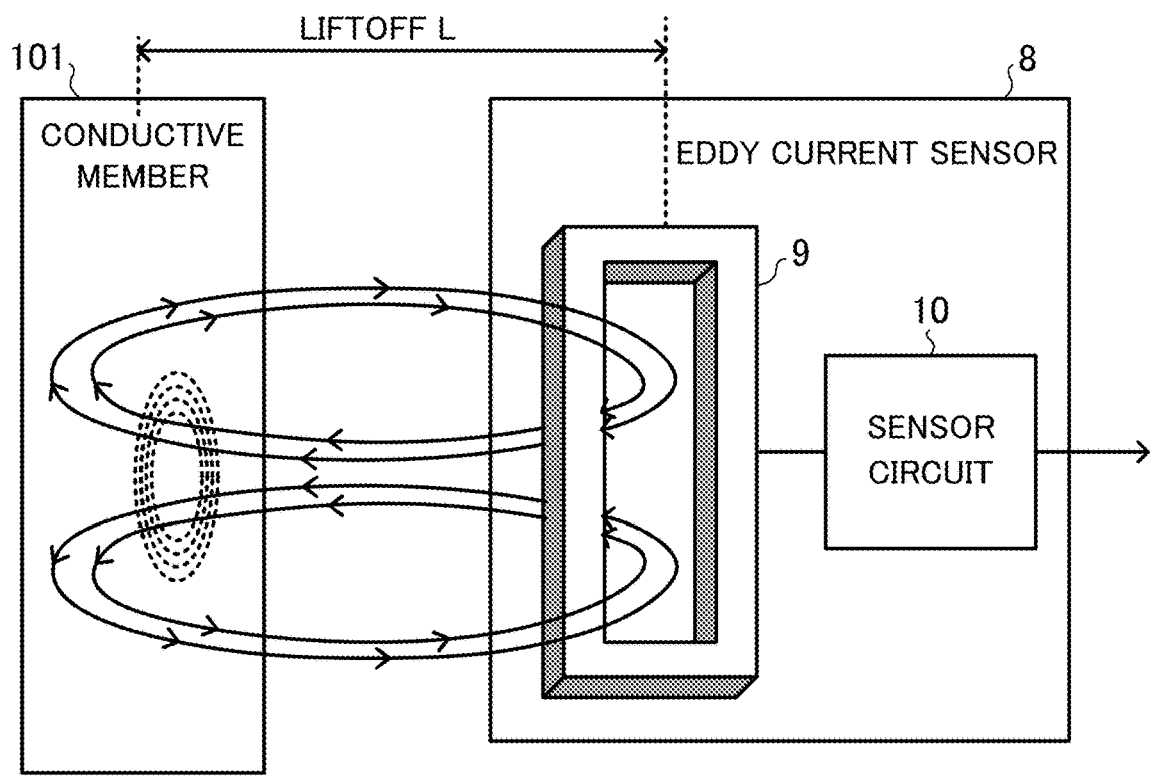
FIG. 4 is a diagram illustrating a configuration of an eddy current sensor.

FIG. 3 is a diagram illustrating an internal configuration of the endoscope. FIG. 4 is a diagram illustrating a configuration of an eddy current sensor. Hereinafter, with reference to FIGS. 3 and 4, a configuration of the endoscope 1 will be described in detail.

As shown in FIG. 3, the endoscope 1 includes a light source part 2, an imaging part 3, a wireless communication part 4, a control part 5, a sensor part 6, and a battery 7 which supplies electric power to each of the parts.

The light source part 2 includes a built-in light source which emits illumination light. Although the built-in light source is not particularly limited, the built-in light source is, for example, a white LED which emits white light for normal observation. In addition, the light source part 2 may include a semiconductor light source which emits special light used for special light observation such as narrow band imaging (NBI) (registered trademark) observation and auto-fluorescence imaging (AFI) (registered trademark) observation. The endoscope 1 may appropriately make switching between the normal observation with the white light and the NBI observation by controlling the light source part 2.

The imaging part 3 includes an image sensor which detects light from a test object 102 which is irradiated with the illumination light. The image sensor is, for example, a charge coupled device (CCD) image sensor, a complementary MOS (CMOS) image sensor, or the like. The imaging part 3 generates an endoscopic image transmitted to the video processor 20.

The wireless communication part 4 transmits and receives signals to and from the video processor 20. Specifically, the wireless communication part 4 transmits, for example, the endoscopic image generated by the imaging part 3 to the video processor 20. It is to be noted that a communication method between the wireless communication part 4 and the video processor 20 is not particularly limited.

The control part 5 controls operation of each of the light source part 2, the imaging part 3, and the wireless communication part 4. In addition, on the basis of a detection result by the sensor part 6, the control part 5 switches an operation mode of the endoscope 1. Specifically, on the basis of a detection result of the conductive member 101 by at least one or more proximity sensors 6a included in the sensor part 6, the control part 5 makes switching between a normal operation mode and an energy-saving operation mode. Thus, the endoscope 1 enables inhibiting useless power consumption in the endoscope 1.

It is to be noted that it is only required for the energy-saving operation mode to be an operation mode of which power consumption is lower than that of the normal operation mode. The control part 5 may dim the illumination light emitted from the light source part 2 in, for example, the energy-saving operation mode so as to be dimmer than the illumination light emitted therefrom in the normal operation mode and may stop emitting of the illumination light from the light source part 2. Thus, electric power consumed by the light source part 2 can be inhibited. In addition, the control part 5 may transfer the endoscopic image obtained by the imaging part 3 from the endoscope 1 to the video processor 20 in, for example, the energy-saving operation mode at an image transfer rate lower than an image transfer rate in the normal operation mode and may stop transferring of the endoscopic image. Thus, electric power consumed by the wireless communication part 4 can be inhibited. In addition, even in the case where the transferring of the endoscopic image is stopped, only minimum operation in which wireless connection between the endoscope 1 and the video processor 20 is maintained, for example, only minimum communication may be performed. In other words, while a state in which the endoscope 1 and the video processor 20 recognize each other as a counterpart of the wireless connection is maintained, the endoscope 1 and the video processor 20 operate so as to save power as much as possible. Thus, since while electric power consumed by the endoscope 1 is inhibited, it is not needed to perform pairing again for reconnection upon resuming image transfer, time required for the pairing can be saved and overhead of communication can be avoided, thereby allowing the image transfer to be early resumed. In addition, the control part 5 may dim the illumination light or stop emitting of the illumination light and may reduce the image transfer rate in, for example, the energy-saving operation mode. As described above, it is desirable that in the energy-saving operation mode, by adjusting operation of at least one of the light source part 2 and the wireless communication part 4, in each of which an amount of the power consumption is comparatively large, the amount of the power consumption is inhibited.

In a case where the image transfer rate is adjusted, in the energy-saving operation mode, the control part 5 may decimate a part of pixels of the endoscopic image obtained by the imaging part 3 and may thereafter transfer the endoscopic image from the endoscope 1 to the video processor 20. Thus, the image transfer rate may be adjusted while a frame rate is maintained. Alternatively, in the energy-saving operation mode, the control part 5 may control the imaging part 3 so as to image the test object at a frame rate lower than a frame rate in the normal operation mode. Thus, electric power consumed by the imaging part 3 in addition to the electric power consumed by the wireless communication part 4 may be inhibited. Furthermore, in the energy-saving operation mode, the control part 5 may control the imaging part 3 so as to image the test object at the frame rate lower than the frame rate in the normal operation mode and may decimate the part of pixels of the endoscopic image obtained by the imaging part 3 and may then transfer the endoscopic image from the endoscope 1 to the video processor 20. It is to be noted that the control part 5 may adjust imaging operation by the imaging part 3 so as not to be in conjunction with adjustment of the image transfer rate and for example, in the energy-saving operation mode, may stop imaging by the imaging part 3.

The sensor part 6 includes one or more proximity sensors 6a, any of which detects the conductive member and a posture sensor 6b. In each of the one or more proximity sensors 6a, an eddy current sensor 8 which detects eddy induced currents generated in the conductive member 101 is included (see FIG. 4). In each of the one or more proximity sensors 6a, other sensor which can detect the conductive member 101 may be included and for example, a capacitance type proximity sensor or the like may be included. The posture sensor 6b is a sensor which detects a posture of the endoscope 1 and includes, for example, a gyroscope sensor, acceleration sensor, and the like.

As shown in FIG. 4, the eddy current sensor 8 includes a sensor coil 9 and a sensor circuit 10. The sensor coil 9 generates an alternating current magnetic flux by a high frequency current supplied from the sensor circuit 10. The sensor circuit 10 detects a current flowing in the sensor coil 9 and generates an output signal.

The eddy current sensor 8 is a sensor which detects change in impedance of the sensor coil 9 by eddy currents generated in the conductive member 101. In the eddy current sensor 8, when the sensor coil 9 and the conductive member 101 come close to each other, a number of cross fluxes penetrating the sensor coil 9 changes by the eddy currents induced by the conductive member 101. Therefore, by detecting the change in the impedance of the sensor coil 9, which is caused by the change in the number of cross fluxes, presence of the conductive member 101 can be detected.

In the endoscope 1 configured as described above, any of the proximity sensors 6a detects the conductive member 41 of the endoscope hanger 40 and the metallic tray 50, whereby the operation mode of the endoscope 1 is switched from the normal operation mode to the energy-saving operation mode. Thus, at timing at which the endoscope 1 is obviously not in use such as in a case where the endoscope 1 is hung on the endoscope hanger 40 and in a case the endoscope 1 is placed on the tray 50, electric power supply can be controlled. Therefore, while necessary electric power is surely supplied, useless power consumption can be surely inhibited. In particular, since in the endoscope 1, by detecting the conductive member, the operation mode can be switched, it is only required for each of a holding tool such as the endoscope hanger and a receiving tool such as the tray, which are used in combination with the endoscope 1, to include a metallic member or the like, and the existing tools can be used as they are.

In addition, in the endoscope 1, each of the proximity sensors 6a includes the eddy current sensor. Because the eddy currents are not induced by a member other than the conductive member, unlike capacitance type proximity sensors or the like, by using the eddy current sensor, a detection target can be limited to the conductive member. Therefore, the endoscope 1 can inhibit a situation in which a member, not intended, is erroneously detected and the operation mode is thereby switched.

Hereinbefore, the exampled in which in the energy-saving operation mode, the operation of each of the light source part 2, the imaging part 3, and the wireless communication part 4 is adjusted is described, and in a case where the operation of the wireless communication part 4 among these is stopped, it is often the case that it takes a long time for return, as compared with a case where the operation of each of the light source part 2 and the imaging part 3 is stopped, and due to this, responsiveness is easily sacrificed. One factor of this is that when the wireless connection between the endoscope 1 and the video processor 20 is once disconnected, before data transfer therebetween is started, additional work for establishing the wireless connection again is required.

Therefore, as to a specific operation mode after switching from the normal operation mode to the energy-saving operation mode, in consideration of balance between inhibition of the power consumption and the responsiveness of the endoscope 1, an operator may select an operation mode from among previously provided operation modes, and on the basis of a remaining amount of the battery 7 or the like, the endoscope 1 may automatically select an operation mode.

A first example of the specific operation mode is that when the endoscope 1 is place on the tray 50 or is hung on the endoscope hanger 40, any of the one or more proximity sensors 6a detects the conductive member 101, and the operation mode is switched to the energy-saving operation mode, the control part 5 immediately stops emitting of the illumination light from the light source part 2 and also stops the imaging operation by the imaging part 3. In addition, concurrently therewith, the control part 5 also disconnects the wireless connection between the wireless communication part 4 and the video processor 20. This operation mode allows the endoscope 1 to inhibit the power consumption at a maximum.

A second example of the specific operation mode is similar to the first example in that when the operation mode is switched to the energy-saving operation mode, the control part 5 immediately stops the emitting of the illumination light from the light source part 2 and also stops the imaging operation by the imaging part 3. Thereafter, when any of the one or more proximity sensors 6a detects the conductive member 101 continuously for a predetermined period of time or more, that is, the energy-saving operation mode is maintained for the predetermined period of time or more, the control part 5 also disconnects the wireless connection between the wireless communication part 4 and the video processor 20. For example, in a case where the operator has once placed the endoscope 1 on the tray 50 but soon resumes using of the endoscope 1, since the wireless connection is not disconnected, this operation mode allows the operator to resume using of the endoscope 1 without inconvenience.

A third example of the specific operation mode is similar to the first example and the second example in that when the operation mode is switched to the energy-saving operation mode, the control part 5 immediately stops the emitting of the illumination light from the light source part 2 and also stops the imaging operation by the imaging part 3. Thereafter, when the energy-saving operation mode is maintained for a predetermined period of time or more, the control part 5 reduces a bit rate between the wireless communication part 4 and the video processor 20. Not only in the case where soon after switching to the energy-saving operation mode, using the endoscope 1 is resumed as in the second example but also in a case where the energy-saving operation mode is maintained for the predetermined period of time or more, this operation mode allows return to setting in normal use only by recovering the bit rate. Therefore, without sacrificing operability of the operator, inhibition in the power consumption can be achieved.

A fourth example of the specific operation mode is similar to the first to the third example in that when the operation mode is switched to the energy-saving operation mode, the control part 5 immediately stops the emitting of the illumination light from the light source part 2 and also stops the imaging operation by the imaging part 3. In addition, the fourth example is similar to the third example in that thereafter, when the energy-saving operation mode is maintained for the predetermined period of time or more, the control part 5 reduces the bit rate between the wireless communication part 4 and the video processor 20. In the present example, when the energy-saving operation mode is maintained further for a second predetermined period of time (>the predetermined period of time) exceeding the predetermined period of time or more, the control part 5 also disconnects the wireless connection between the wireless communication part 4 and the video processor 20. In other words, the control part 5 inhibits the power consumption in the wireless communication part 4 via the reduction in the bit rate to the disconnection of the wireless connection in a stepwise manner. This operation mode allows balancing between the operability of the operator and the inhibition in the power consumption at a further high level.

Another operation mode may be an operation mode in which the stopping of the emitting of the illumination light in the first to the fourth example is changed to dimming of the illumination light. In addition, still another operation mode may be an operation mode in which the stopping of the imaging operation in each of the first to the fourth example is changed to a reduction in a frame rate. In addition, yet another operation mode may be an operation mode in which the stopping of the imaging operation in the first to the fourth example is changed to decimating of a part of pixels from the image. In addition, further another operation mode may be any combination of these.

Hereinafter, a desirable aspect of the endoscope 1 will be described. First, it is desirable that a coil diameter of the sensor coil 9 is larger than an internal diameter of a forceps port which opens at a leading end of the insertion part 13 of the endoscope 1. In addition, it is further desirable that the coil diameter of the sensor coil 9 is three times or more as large as the internal diameter of the forceps port. This is because the internal diameter of the forceps port is deemed to substantially define a size of a treatment tool guided to the test object via the forceps port, and this is to avoid switching the operation mode to the energy-saving operation mode by detecting the treatment tool formed of the conductive member. Further details will be as follows.

Because the shorter a distance between the sensor coil 9 and the conductive member 101 (hereinafter, referred to as a liftoff L and see FIG. 4) is, the larger change in impedance is caused in the sensor coil 9, in the eddy current sensor 8, output in accordance with the liftoff L can be obtained. On the other hand, as described in Journal of Magnetics Society of Japan, pages 569-572, Vol. 20, No. 2, 1996, when the liftoff L is constant, output in accordance with an area ratio between a coil area calculated from the coil diameter of the sensor coil 9 and an area of a surface facing the sensor coil 9 of the conductive member 101 (hereinafter, referred to as a target area) is obtained, and the smaller the target area/coil area is, the smaller also the change in the impedance is. In particular, since in a range in which the liftoff L is small, as compared with the coil diameter, change in inductance (eventually, the change in the impedance) strongly depends on an area of the conductive member 101, detection sensitivity of the eddy current sensor 8 having the sensor coil 9 of which coil diameter is large is lowered. Therefore, it is difficult to detect a target of which diameter is smaller than the coil diameter, and in general, it is desirable that a diameter of a plane surface of a target is three times or more as large as the coil diameter. This is because when the diameter of the plane surface exceeds three times the coil diameter, the change in the impedance is approximately constant, not depending on the area ratio, and as a result, the detection sensitivity is also approximately constant at a high level.

The above-described characteristics regarding the coil diameter which the eddy current sensor 8 of the endoscope 1 has are largely different from those of the conventional eddy current sensor. In order to surely detect even a small target by the eddy current sensor, it is desirable that the coil diameter is small, and this agrees with requisition to sensors in general, which are desired to be small-sized and lightweight. In contrast to this, as opposed to the above-mentioned requisition in general, by intendedly designing the coil diameter of the sensor coil 9 to be large, the eddy current sensor 8 of the endoscope 1 limits a detection target. By designing the eddy current sensor 8 as described above, the endoscope 1 makes it possible to further ensure a function to surely supply the electric power required when the endoscope is used.

It is to be noted that although in FIG. 4, an example in which the coil is wound in a rectangle is shown, a shape of the coil is not particularly limited. It is only required for the shape of the coil to generate a magnetic flux, and the coil may be wound in, for example, any annular shape such as a circular shape and an elliptic shape. In addition, in the present description, the coil diameter is a distance from an axis of the coil to the coil, and in a case where the coil has a certain thickness, the coil diameter may be, for example, a distance from the axis of the coil to the center of the thickness of the coil. More specifically, by integrating the distance from the axis of the coil to the coil along the coil and dividing a value obtained by the integration by a length of the coil, the coil diameter may be calculated. It is to be noted that the axis of the coil may be defined by, for example, the center of gravity of a projected image of the coil and a normal vector, the projected image obtained when the coil is projected on a plane surface having the normal vector in a direction orthogonal to the magnetic flux generated in the coil, and in a case where the coil is wound in the circular shape, aggregate of centers of circles is the axis of the coil.

In addition, the sensor coil 9 may be featured by the coil area, instead of the coil diameter, and in such a case, it is desirable that the coil area of the sensor coil 9 is larger than a sectional area of the forceps port which opens at the leading end of the insertion part 13 of the endoscope 1. It is to be noted that also by designing the sensor coil 9 as described above, the endoscope 1 makes it possible to further ensure the function to surely supply the required electric power.

Figure 5:
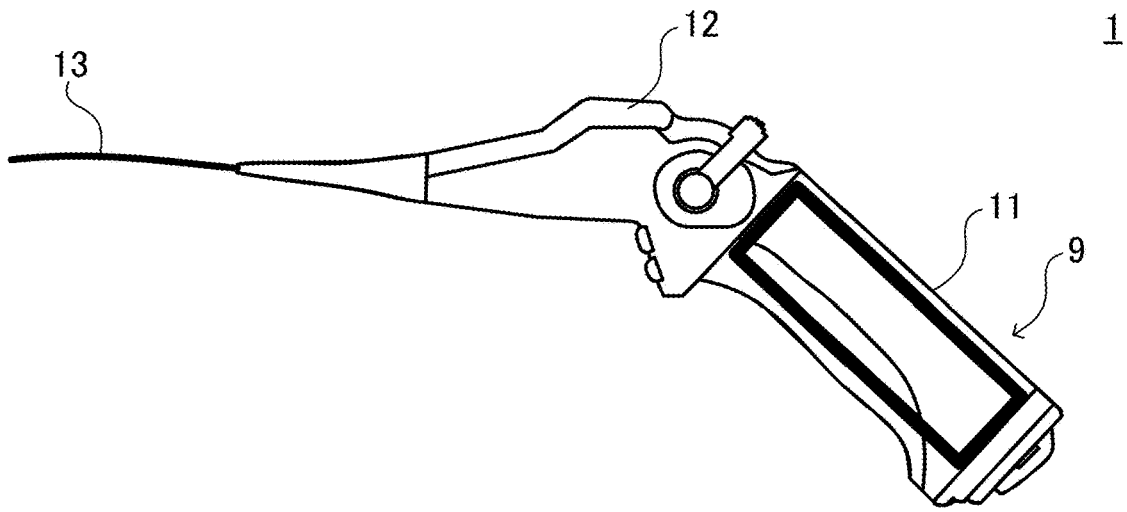
FIG. 5 is a diagram showing one example of placement of a sensor coil.
Figure 6:
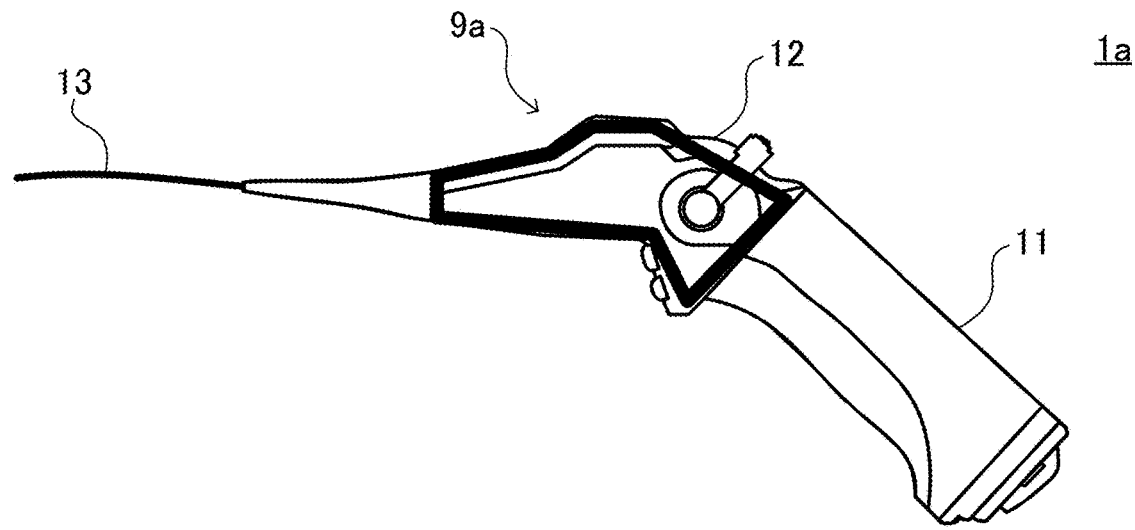
FIG. 6 is a diagram showing another example of the placement of the sensor coil.
Figure 7:
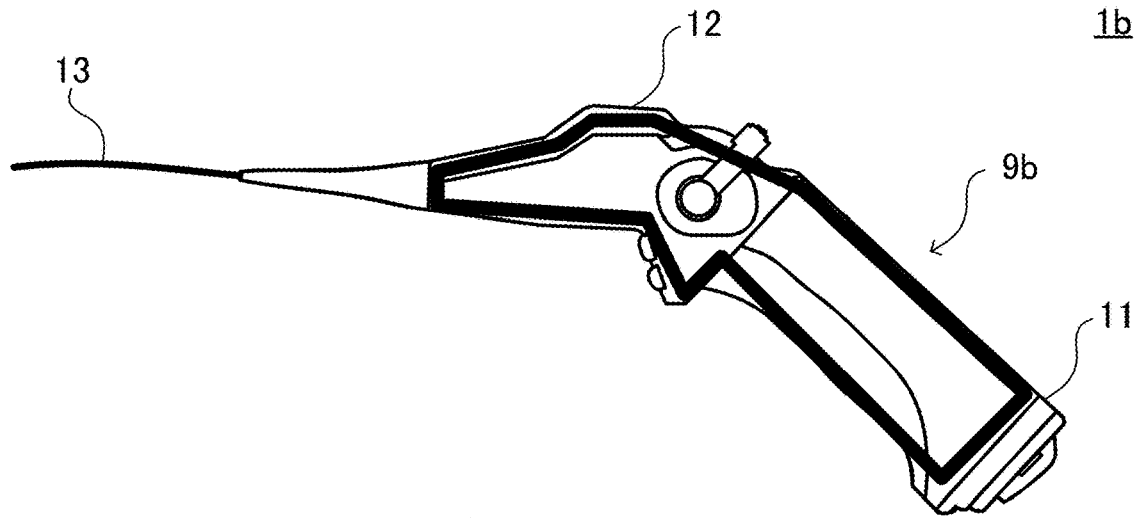
FIG. 7 is a diagram showing still another example of the placement of the sensor coil.
Figure 8:
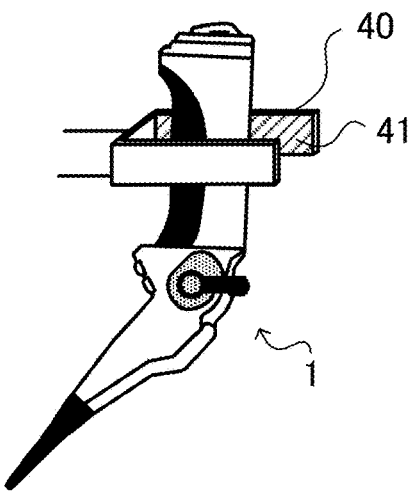
FIG. 8 is diagram showing one example of a holding form of the endoscope on an endoscope hanger.
Figure 9:
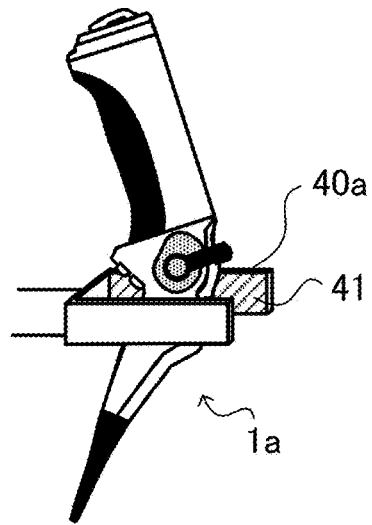
FIG. 9 is a diagram showing another example of the holding form of the endoscope on the endoscope hanger.

FIGS. 5, 6, and 7 are diagrams showing variations of placement of the sensor coil. In addition, FIGS. 8 and 9 are diagrams showing variations of a holding form of the endoscope on the endoscope hanger. Hereinafter, with reference to FIGS. 5 to 9, desirable placement of the sensor coil will be described.

In the endoscope 1 shown in FIG. 5, the sensor coil 9 is provided in the grip part 11 of the endoscope 1. In addition, in order to realize a large coil diameter, the sensor coil 9 is wound along a contour shape of the grip part 11. In more details, the sensor coil 9 is wound such that the axis of the sensor coil 9 faces a direction intersecting a tray bottom surface when the endoscope 1 is placed on the tray 50. In the above-described placement, when the endoscope 1 is placed on the tray 50, switching to the energy-saving operation mode is surely made. Furthermore, since in general, the treatment tool is inserted into the endoscope 1 from the forceps port provided for the operation part 12, the treatment tool does not come close to the sensor coil 9 and accordingly, erroneously detecting the treatment tool and thereby switching to energy-saving operation mode can also be surely avoided. In addition, although in a case where the endoscope 1 is an industrial endoscope, it is assumed that a test object itself is a conductive member, by providing the sensor coil 9 in the grip part 11, even if the test object is the conductive member, detecting the test object by the eddy current sensor 8 and thereby switching to the energy-saving operation mode can be avoided. It is to be noted that in a case where a plurality of postures in which the endoscope 1 is stable when the endoscope 1 is placed on the tray 50 is present, a plurality of sensor coils may be provided in the grip part 11 and the plurality of sensor coils may be wound such that any axis of the plurality of sensor coils faces a direction intersecting the tray bottom surface when the endoscope 1 is placed on the tray 50 in each of the postures.

An endoscope 1a shown in FIG. 6 is different from the endoscope 1 in that a sensor coil 9a is provided in an operation part 12 of the endoscope 1a. The endoscope 1a is similar to the endoscope 1 in other points. It is to be noted that in order to realize a large coil diameter, the sensor coil 9a is wound along a contour shape of the operation part 12. In more details, the sensor coil 9a is wound such that an axis of the sensor coil 9a faces a direction intersecting the tray bottom surface when the endoscope 1a is placed on the tray 50. In the above-described placement, when the endoscope 1a is placed on the tray 50, switching to the energy-saving operation mode is surely made. Furthermore, since probability with which a wristwatch, a finger ring, and the like which an operator wears come close to the sensor coil 9a is lowered, erroneously detecting these and thereby switching to the energy-saving operation mode can also be avoided. It is to be noted that in a case where a plurality of postures in which the endoscope 1a is stable when the endoscope 1a is placed on the tray 50 is present, a plurality of sensor coils may be provided in the operation part 12 and the plurality of sensor coils may be wound such that any axis of the plurality of sensor coils faces a direction intersecting the tray bottom surface when the endoscope 1a is placed on the tray 50 in each of the postures.

An endoscope 1b shown in FIG. 7 is different from the endoscope 1 in that a sensor coil 9b is provided over from a grip part 11 of the endoscope 1b to the operation part 12. The endoscope 1b is similar to the endoscope 1 in other points. It is to be noted that the sensor coil 9b is wound along contour shapes of the grip part 11 and the operation part 12. In more details, the sensor coil 9b is wound such that an axis of the sensor coil 9b faces a direction intersecting the tray bottom surface when the endoscope 1b is placed on the tray 50. In the above-described placement, when the endoscope 1b is placed on the tray 50, switching to the energy-saving operation mode is surely made. Furthermore, since a coil diameter becomes sufficiently large, erroneously detecting a wristwatch and a finger ring which an operator wears and a treatment tool and the like which the operator operates and thereby switching to the energy-saving operation mode can be avoided. It is to be noted that in a case where a plurality of postures in which the endoscope 1b is stable when the endoscope 1b is placed on the tray 50 is present, a plurality of sensor coils may be provided over from the grip part 11 to the operation part 12 and the plurality of sensor coils may be wound such that any axis of the plurality of sensor coils faces a direction intersecting the tray bottom surface when the endoscope 1b is placed on the tray 50 in each of the postures.

In the case where the sensor coil 9 is provided in the grip part 11, it is desirable that the endoscope system 100 includes an endoscope hanger 40 which is of a type of holding the grip part 11 as shown in FIG. 8. Thus, since when the endoscope 1 is hung on the endoscope hanger 40, the conductive member 41 is detected by the eddy current sensor 8 of the endoscope 1, the operation mode can be switched to the energy-saving operation mode.

In addition, in the case where the sensor coil 9a is provided in the operation part 12, it is desirable that the endoscope system 100 includes an endoscope hanger 40a which is of a type of holding the operation part 12 as shown in FIG. 9. Thus, since when the endoscope 1 is hung on the endoscope hanger 40a, the conductive member 41 is detected by the eddy current sensor 8 of the endoscope 1a, the operation mode can be switched to the energy-saving operation mode.

It is to be noted that in the case where the sensor coil 9b is provided over from the grip part 11 to the operation part 12, the endoscope system 100 may include the endoscope hanger 40 which is of the type of holding the grip part 11 as shown in FIG. 8 or may include the endoscope hanger 40a which is of the type of holding the operation part 12 as shown in FIG. 9. Even in either case, since when the endoscope 1b is hung on the endoscope hanger, the conductive member 41 is detected by the eddy current sensor 8 of the endoscope 1b, the operation mode can be switched to the energy-saving operation mode.

Figure 10:
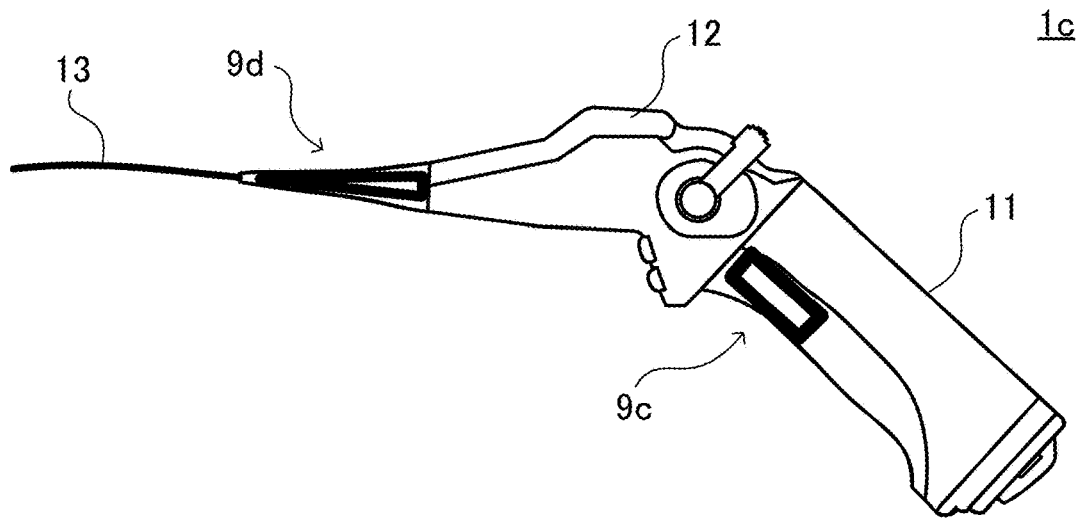
FIG. 10 is a diagram showing further another example of the placement of the sensor coil.
Figure 11:
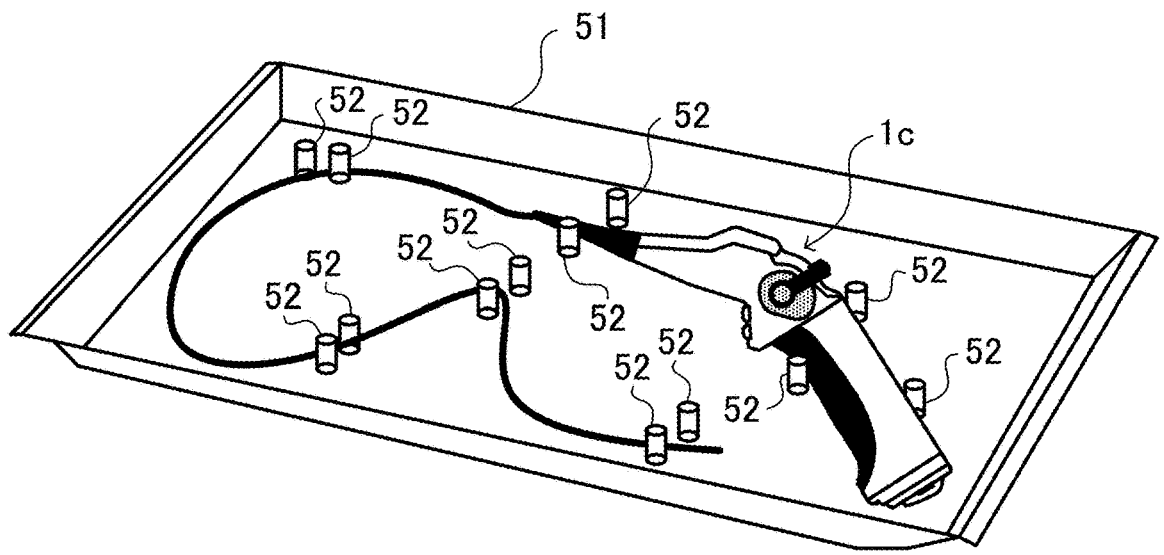
FIG. 11 is a diagram showing another example of a tray on which the endoscope is placed.

FIG. 10 is a diagram showing further another example of the placement of the sensor coil. FIG. 11 is a diagram showing another example of the tray on which the endoscope is placed. Hereinafter, with reference to FIGS. 10 and 11, placement of a sensor coil which is particularly desirable in a case where a nonmetallic tray is used will be described.

An endoscope 1c shown in FIG. 10 includes two eddy current sensors. A sensor coil 9c of one of the eddy current sensors is provided in an inside of a grip part 11, that is, a portion which contacts first joints and second joints of fingers when an operator grips the grip part 11. In addition, a sensor coil 9d of the other of the eddy current sensors is provided in a boundary portion between an operation part 12 and an insertion part 13. Either of the sensor coils is wound such that an axis of each of the sensor coils faces a direction substantially in parallel with a tray bottom surface when the endoscope 1c is placed on a nonmetallic tray 51. In the above-described placement, as shown in FIG. 11, since metallic pins 52 which are provided for a tray 51 to fix the endoscope 1c in a predetermined position when the endoscope 1c is placed on the tray 51 are detected by the eddy current sensors, switching to an energy-saving operation mode is surely made. It is to be noted that the tray having the metallic pins 52 is not limited to the nonmetallic tray and may be a metallic tray.

Figure 12:
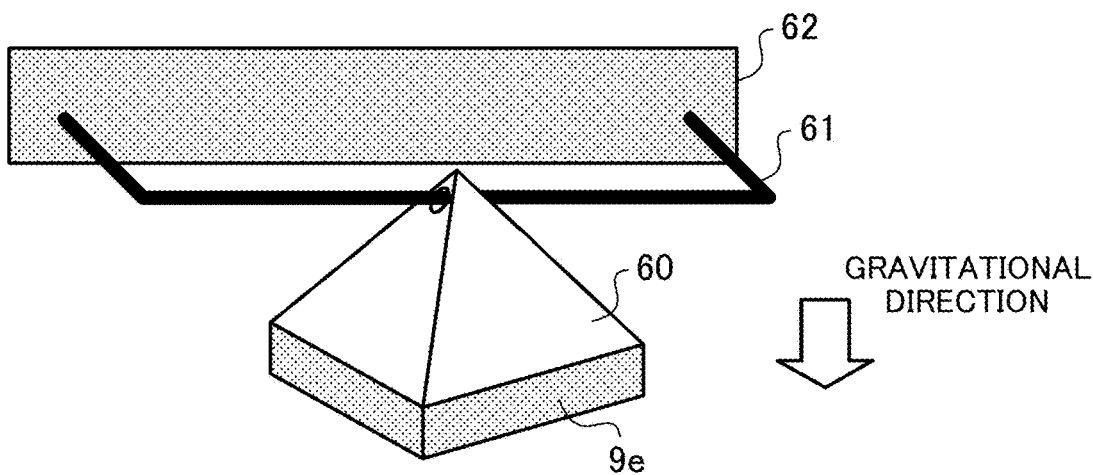
FIG. 12 is a diagram exemplifying a structure for adjusting a direction of the sensor coil.
Figure 12:
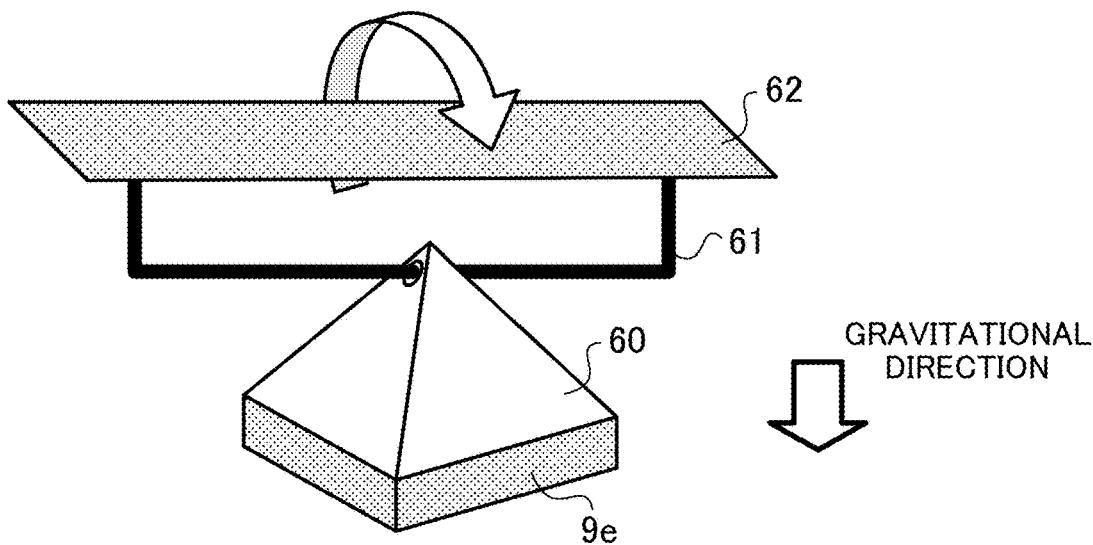

It is to be noted that although hereinbefore, the examples in which the sensor coil or sensor coils are fixed inside the endoscope are described, the sensor coil may be provided in such a way as to turn inside the endoscope depending on a posture of the endoscope. For example, as shown in FIG. 12, a sensor coil 9e may be fixed on a bottom surface of a weight 60, and the sensor coil 9e may be configured such that an axis of the sensor coil 9e invariably faces a gravitational direction by passing a supporting member 61 fixed on a wall surface 62 of the endoscope through a through hole provided for the weight 60. Thus, in a case where the endoscope is placed on the tray 50, facing even any direction, since eddy currents can be surely induced on a bottom surface of the tray, the tray is detected and the operation mode can be thereby switched to the energy-saving operation mode.

The above-described embodiment shows specific examples for facilitating understanding of the present disclosure, and the embodiment of the present disclosure is not limited to these. A variety of modifications and changes to the endoscope and the method for operating the endoscope can be devised without departing from the scope of the description of the claims.

For example, at least a region of a surface of the endoscope, through which the magnetic flux generated from the sensor coil pass, may be subjected to water repellent finish. Thus, occurrence of a situation in which the eddy current sensor detects human body fluid having high electric conductivity and as a result, during observation of an inside of a body cavity, the operation mode is switched to the energy-saving operation mode can be inhibited.

In addition, in the above-described embodiment, the example in which any of the one or more proximity sensors 6a detects the conductive member and switching to the energy-saving operation mode is thereby made is shown. However, when each of a plurality of proximity sensors 6a included in the one or more proximity sensors 6a detects the conductive member, the control part 5 may switch the operation mode to the energy-saving operation mode. By switching the operation mode on condition that the plurality of proximity sensors 6a detect the conductive member, probability with which for example, by detecting a conductive member such as a finger ring, which is not intended, switching of the operation mode is made can be substantially reduced.

In the above-described embodiment, the example in which any of the one or more proximity sensors 6a detects the conductive member and in which the operation mode is switched to the energy-saving operation mode is shown. However, when any of the one or more proximity sensors 6a detects the conductive member continuously for a predetermined period of time or more, the control part 5 may switch the operation mode to the energy-saving operation mode. As described above, by providing a certain grace period for switching the operation mode, risk that at timing which is not intended by an operator, switching to the energy-saving operation mode is made can be substantially reduced. It is to be noted that the certain grace period may be applied only in a case where switching from the normal operation mode to the energy-saving operation mode is made, and no grace period may be provided in a case where switching from the energy-saving operation mode to the normal operation mode is made. By using such an unsymmetrical switching criterion, both of inhibiting useless power consumption and surely supplying necessary electric power can be achieved at a high level. It is to be noted that switching from the energy-saving operation mode to the normal operation mode may be made by manual operation of an operator or may be made on the basis of the detection result of the proximity sensors as with the switching from the normal operation mode to the energy-saving operation mode. Specifically, return from the energy-saving operation mode to the normal operation mode may be made by pressing down a specific switch provided for the endoscope, or the return from the energy-saving operation mode to the normal operation mode may be made when a state in which the proximity sensors are detecting the conductive member is changed to a state in which the proximity sensors are not detecting the conductive member.

In the above-described embodiment, the example in which any of the one or more proximity sensors 6a detects the conductive member and in which the operation mode is switched to the energy-saving operation mode is shown. Specifically, shown are the example in which the control part 5 switches the operation mode to the energy-saving operation mode in the case where the detection result of the conductive member by the one or more proximity sensors 6a is the result obtained when the endoscope 1 is placed on the metallic tray 50; the example in which the operation mode is switched to the energy-saving operation mode in the case where the detection result of the conductive member by the one or more proximity sensors 6a is the result obtained when the endoscope is placed on the nonmetallic tray 51 including the metallic pins 52 to fix the endoscope in the predetermined position; the example in which the operation mode is switched to the energy-saving operation mode in the case where the detection result of the conductive member by the one or more proximity sensors 6a is the result obtained when the endoscope is hung on the metallic endoscope hanger 40; and the like. However, on the basis of the detection result of the conductive member by the one or more proximity sensors 6a and the detection result of the posture of the endoscope 1 by the posture sensor 6b, the control part 5 may make switching between the normal operation mode and the energy-saving operation mode. More specifically, for example, in a case where any of the one or more proximity sensors 6a detects the conductive member and the posture sensor 6b detects a predetermined posture, the control part 5 may switch the operation mode to the energy-saving operation mode. Since by combining the proximity sensors 6a and the posture sensor 6b, probability with which an unused state of the endoscope 1 is erroneously detected can be decreased, necessary electric power can be further surely supplied. It is to be noted that although herein, as one example of the conductive member, each of the metallic tray, the metallic pins, and the metallic hanger is exemplified, the conductive member is not limited to metal. The conductive member may be, for example, made of carbon, resin with conductive particles added, or the like. Accordingly, instead of the metallic tray, a tray made of carbon or a tray made of Teflon (registered trademark) with conductive particles added may be used, and instead of the metallic pins, pins made of resin with conductive particles added may be provided. In addition, the pins provided for the tray may be pins with surrounding of metallic pins covered with Teflon.

Although the detection result of the conductive member by the proximity sensors 6a is outputted, for example, as a voltage value from the proximity sensors 6a to the control part 5, the voltage value (a threshold voltage) that the control part 5 should determine that the conductive member is detected may be adjusted by an operator in consideration of a previously assumed liftoff, a target area, and the like. In addition, the conductive member may be detected by using threshold voltages which are different from each other between when the endoscope is hung on the endoscope hanger 40 and when the endoscope is placed on the tray 50, and in this case, the control part 5 may determine a threshold voltage which should be used on the basis of the detection result of the posture sensor 6b.

In addition, although in the above-described embodiment, the example in which in FIG. 10, both of the two eddy current sensors are provided for the purpose of detecting the pins 52 is shown, the plurality of proximity sensors provided for the endoscope may be provided for the purpose of detecting different targets. For example, one or more proximity sensors may be provided for detecting the tray, alternate one or more proximity sensors may be provided for detecting the pins provided for the tray, and further alternate one or more proximity sensors may be provided for detecting the endoscope hanger.

What is claimed is:

1. An endoscope comprising:
    an eddy current sensor that is configured to detect a conductive member by detecting eddy induced currents generated in the conductive member, the eddy current sensor including (i) a sensor coil having a coil diameter that is larger than an internal diameter of a forceps port that opens at a leading end of an insertion part of the endoscope and being configured to generate an alternating current magnetic flux, and (ii) a sensor circuit configured to supply a current with a frequency to the sensor coil, detect a change in impedance in the sensor coil, and output a signal based on the change in impedance; and
    a processor configured to switch between a normal operation mode and an energy-saving operation mode in which power consumption is smaller than power consumption in the normal operation mode, based on the signal output by the sensor circuit.

2. The endoscope according to claim 1, wherein the coil diameter is at least three times larger than the internal diameter of the forceps port.

3. The endoscope according to claim 1, wherein the sensor coil is provided in a grip part of the endoscope, the grip part being configured to be gripped by an operator.

4. The endoscope according to claim 1, wherein the sensor coil is provided in an operation part of the endoscope, the operation part being configured to be operated by an operator.

5. The endoscope according to claim 1, wherein the sensor coil extends from a grip part of the endoscope to an operation part of the endoscope, the grip part being configured to be gripped by an operator, the operation part being configured to be operated by the operator.

6. The endoscope according to claim 1, wherein at least a region of a surface of the endoscope, through which a magnetic flux generated from the sensor coil passes, is subjected to water repellent finish.

7. The endoscope according to claim 1, wherein the processor is configured to:
    dim illumination light emitted from a light source in the energy-saving operation mode so as to be dimmer than illumination light emitted in the normal operation mode, or
    stop emission of the illumination light from the light source in the energy-saving operation mode.

8. The endoscope according to claim 1, further comprising
    an imaging part that is configured to image a test object,
    wherein in the energy-saving operation mode, the processor is configured to:
    transfer an endoscopic image obtained by the imaging part from the endoscope to a video processor at an image transfer rate lower than an image transfer rate in the normal operation mode, or
    stop transfer of the endoscopic image obtained by the imaging part.

9. The endoscope according to claim 1, further comprising
    an imaging part that is configured to image a test object,
    wherein in the energy-saving operation mode, the processor is configured to decimate a part of pixels of an endoscopic image obtained by the imaging part and thereafter, transfer the endoscopic image from the endoscope to a video processor.

10. The endoscope according to claim 1, further comprising
    an imaging part that is configured to image a test object,
    wherein in the energy-saving operation mode, the processor is configured to:
    control the imaging part to image the test object at a frame rate lower than a frame rate in the normal operation mode, or
    stop imaging by the imaging part.

11. The endoscope according to claim 1, wherein the processor is configured to switch an operation mode to the energy-saving operation mode when the eddy current sensor detects the conductive member.

12. The endoscope according to claim 1, wherein the processor is configured to switch an operation mode to the energy-saving operation mode when the eddy current sensor detects the conductive member continuously for a predetermined period of time or more.

13. The endoscope according to claim 1, further comprising
    a posture sensor that is configured to detect a posture of the endoscope,
    wherein the processor is further configured to switch between the normal operation mode and the energy-saving operation mode based on the detection result of the conductive member by the eddy current sensor and a detection result of the posture of the endoscope by the posture sensor.

14. The endoscope according to claim 1, further comprising:
    a light source part that is configured to emit illumination light;
    a wireless communication part that is configured to wirelessly transfer an endoscopic image to a video processor; and
    a battery that is configured to supply electric power to at least the light source part and the wireless communication part.

15. The endoscope according to claim 1, further comprising
    a wireless communication part that is configured to wirelessly transfer an endoscopic image to a video processor,
    wherein in the energy-saving operation mode, the wireless communication part is configured to disconnect wireless connection or stop image transfer while the wireless connection between the endoscope and the video processor is maintained.

16. The endoscope according to claim 1, further comprising
    a wireless communication part that is configured to wirelessly transfer an endoscopic image to a video processor,
    wherein in the energy-saving operation mode, the wireless communication part is configured to limit communication while maintaining a state in which the endoscope and the video processor recognize each other as a counterpart of wireless connection.

17. A method for operating an endoscope, the method comprising:
- detecting, by one or more eddy current sensors included in the endoscope, a conductive member, the one or more eddy current sensors being configured to detect the conductive member by detecting eddy induced currents generated in the conductive member, each eddy current sensor including (i) a sensor coil having a coil diameter that is larger than an internal diameter of a forceps port that opens at a leading end of an insertion part of the endoscope and being configured to generate an alternating current magnetic flux, and (ii) a sensor circuit configured to supply a current with a frequency to the sensor coil, detect a change in impedance in the sensor coil, and output a signal based on the change in impedance; and
- switching, by a control part comprised by the endoscope, between a normal operation mode and an energy-saving operation mode in which power consumption is smaller than power consumption in the normal operation mode based on the signal output by the sensor circuit.

18. The method according to claim 17, wherein
the control part switches an operation mode to the energy-saving operation mode when the one or more eddy current sensors detects the conductive member due to the endoscope being placed on a tray having conductivity or a tray including the conductive member added thereto.

19. The method according to claim 17, wherein
an operation mode is switched to the energy-saving operation mode when the one or more eddy current sensors detects the conductive member due to the endoscope being placed on a tray including pins having conductivity to fix the endoscope in a predetermined position or pins with the conductive member added thereto.

20. The method according to claim 17, wherein
an operation mode is switched to the energy-saving operation mode when the one or more eddy current sensors detects the conductive member due to the endoscope being hung on an endoscope hanger having conductivity.

* * * * *